US007121098B2

(12) United States Patent
Hatcher

(10) Patent No.: US 7,121,098 B2
(45) Date of Patent: Oct. 17, 2006

(54) HIGH-TEMPERATURE INSPECTION DEVICE AND COOLING APPARATUS THEREFOR

(75) Inventor: Clifford Hatcher, Pittsburgh, PA (US)

(73) Assignee: Siemens Power Generation, Inc., Orlando, FL (US)

( * ) Notice: Subject to any disclaimer, the term of this patent is extended or adjusted under 35 U.S.C. 154(b) by 370 days.

(21) Appl. No.: 10/738,837

(22) Filed: Dec. 17, 2003

(65) Prior Publication Data

US 2004/0216468 A1 Nov. 4, 2004

Related U.S. Application Data

(60) Provisional application No. 60/466,478, filed on Apr. 30, 2003.

(51) Int. Cl.
*F25B 9/02* (2006.01)
*A61B 1/04* (2006.01)
*A61B 18/18* (2006.01)

(52) U.S. Cl. ............................ 62/5; 600/109; 600/140; 606/15; 606/46; 385/117

(58) Field of Classification Search ...................... 62/5; 600/109, 140, 157; 431/13; 385/117; 606/15, 606/7, 13, 14, 46
See application file for complete search history.

(56) References Cited

U.S. PATENT DOCUMENTS 4,991,957 A 2/1991 Sakamoto et al.
5,096,292 A 3/1992 Sakamoto et al.

FOREIGN PATENT DOCUMENTS

JP 02017024 A * 1/1990

OTHER PUBLICATIONS

Bates, Stephen and Pollack Michael “Gas Cooled Probe Protectors”, Sep. 1999, SPIE vol. 3852, pp. 113-123.*
Everest VIT, Inc., XL Pro Videoprobe, “No other inspection tool even comes close . . . ”, Sales Brochure, pp. 1-4.
EXAIR, “A Phenomenon of Physics: How the Vortex Tube Works”, pp. 1-3.

* cited by examiner

*Primary Examiner*—Chen Wen Jiang

(57) ABSTRACT

An inspection system includes a cooling apparatus for conducting visual inspections within operating temperature environments, such as, for example, the interior of a combustion turbine shortly after shut down. The cooling apparatus provides cooling for an inspection probe such as a video borescope. The cooling apparatus includes an articulating guide tube having a control portion, an elongate flexible portion and an articulating section. The video borescope is inserted down through the articulating guide tube. A thermal protective sleeve surrounds and thermally insulates a portion of the articulating guide tube. Vortex coolers circulate cooled, compressed air within the cooling apparatus, thereby maintaining a cool video borescope operating temperature.

18 Claims, 5 Drawing Sheets

32

58

58

HIGH-TEMPERATURE INSPECTION DEVICE AND COOLING APPARATUS THEREFOR

CROSS-REFERENCE TO RELATED APPLICATION

This application claims priority under 35 USC § 119(e) to Provisional Application Ser. No. 60/466,478, filed on Apr. 30, 2003, entitled "High-Temperature Inspection Device," explicitly incorporated herein by reference.

BACKGROUND OF THE INVENTION

1. Field of the Invention

The present invention relates generally to visual inspection equipment and, more particularly, to a high-temperature inspection device employing a cooling apparatus, which enables continuous inspecting operations within high-temperature environments for extended periods of time. The invention also relates to cooling apparatus for high-temperature inspection devices.

2. Background Information

Inaccessible or confined areas such as, for example, the internal parts of power industry components (e.g., without limitation, combustors; compressors; turbines; power generation tubes), often require routine inspection to maintain safe operating conditions, to detect a potential problem before it develops into a dangerous condition and to search for and pinpoint the source of an existing problem, such as, for example, lodged debris or a malfunctioning or broken component such as a turbine blade or vane, in order that necessary repairs can be promptly made.

Visual inspection devices such as, for example, electronic or video borescopes are typically used to visually inspect such otherwise inaccessible areas. For example, in order to avoid partial or complete disassembly of the structure of a combustion or steam turbine to conduct a routine or maintenance inspection, a video borescope may be inserted through an inspection port in the turbine, in order to enable the visual observation of the condition of internal parts.

An example of a typical industrial borescope apparatus is disclosed in U.S. Pat. No. 5,096,292. As shown in FIG. 1, such apparatus typically include an electronic borescope 2 and an image processing system 12. The electronic borescope 2 includes an operating section 4 and an elongated insertion section 6 having a flexible tube portion 8 extending therefrom. An optical system, such as, for example, an articulating video system 10 is attached to the distal end of the flexible tube portion 8 and connected to the image processing system 12 by electronic cable 14. The operating section 4 includes a controlling mechanism 16 for adjusting the articulating video system 10, in order to conduct a visual inspection. A compressor 18 and an air hose 20 may optionally be used to supply compressed air to a jet port 22, in order to move or stabilize the elongated insertion section 6.

Such prior art electronic borescope systems and the video inspection equipment associated therewith cannot withstand high temperatures. Accordingly, until now, when internal combustion turbine components needed to be visually inspected or monitored, it was necessary to first cool the turbine to a temperature below approximately 150° F. (66° C.) before inserting the borescope to begin the inspection. This is an expensive and time-consuming process. For example, approximately 12 to 24 hours of cooling time are required to shut down and cool the combustion turbine from its operating temperature of approximately 800° F. (427° C.), to a temperature below approximately 150° F. (66° C.), at which video inspection equipment can withstand continuous inspection operations for extended periods of time. Upwards of approximately 120 hours may be necessary to shut down and cool a steam turbine.

There is a need therefore, for a high-temperature visual inspection system capable of operating continuously within high-temperature environments for extended periods of time.

Accordingly, there is room for improvement in cooling apparatus for visual inspection equipment and in visual inspection equipment employing cooling apparatus.

SUMMARY OF THE INVENTION

These needs and others are satisfied by the present invention, which is directed to a high-temperature inspection device including a unique cooling apparatus enabling the hot visual inspection of internal combustion turbine components immediately following shut down and as soon as the turbine's inspection ports are opened, thereby eliminating a lengthy and expensive cooling down time.

As one aspect of the invention, a cooling apparatus is used with an inspection probe. The inspection probe comprises: an articulating guide tube having a control portion, an elongated flexible portion and an articulating section, the control portion including a first end, a second end and a first interior portion, the elongated flexible portion including an exterior and a second interior portion; a thermal protective sleeve surrounding the elongated flexible portion of the articulating guide tube and including a third interior portion; an inlet formed within the first end of the control portion and structured to receive the inspection probe, in order that the inspection probe may be guided down the first interior portion, through the second interior portion and into the articulating section of the articulating guide tube; and at least one vortex cooler adapted to cool and circulate a compressed fluid thereby cooling both the articulating guide tube and the inspection probe therein.

Each of the at least one vortex cooler may further include at least one inlet nozzle for receiving the compressed fluid, and the articulating guide tube may further include at least one exhaust vent for regulating the compressed fluid.

The compressed fluid may include compressed air. The at least one vortex cooler may include first and second vortex coolers proximate the first and second ends, respectively, of the control portion of the articulating guide tube; wherein the first vortex cooler may form a first outer, rotating airstream and a first cooler, inner airstream, the first cooler, inner airstream blowing over the inspection probe and through the first and second interior portions, respectively, of the articulating guide tube; wherein the second vortex cooler may form a second outer, rotating airstream and a second cooler, inner airstream, the second cooler, inner airstream blowing through the third interior portion of the thermal protective sleeve and over the exterior of the elongated flexible portion of the articulating guide tube; wherein the first and second cooler, inner airstreams may transfer heat to the first and second outer rotating airstreams, respectively; and wherein at least a portion of the heat transferred to the first and second outer rotating airstreams may be exhausted through the at least one exhaust vent in the articulating guide tube.

As another aspect of the invention an inspection system comprises: a compressed fluid source supplying a compressed fluid; a video borescope; an image processing system for processing images viewed through the video borescope; and a cooling apparatus for cooling the video borescope, the cooling apparatus comprising: an articulating guide tube having a control portion, an elongated flexible portion and an articulating section, the control portion including a first end, a second end and a first interior portion, the elongated flexible portion including an exterior and a second interior portion; a thermal protective sleeve surrounding the elongated flexible portion of the articulating guide tube and including a third interior portion; an inlet formed within the first end of the control portion, the inlet receiving the video borescope, which passes down through the first interior portion, through the second interior portion and into the articulating section of the articulating guide tube; and at least one vortex cooler cooling and circulating the compressed fluid thereby cooling both the articulating guide tube and the video borescope therein.

Each of the at least one vortex cooler may further include at least one inlet nozzle receiving the compressed fluid. The compressed fluid source may include at least one air compressor and the compressed fluid may be compressed air. Each of the at least one air compressor may include at least one air hose feeding the compressed air through each of the at least one nozzle and into the at least one vortex cooler.

The articulating section of the articulating guide tube may form an opening for video borescope viewing therethrough. The articulating section and the opening therein may provide full-way articulation to permit 360° viewing through the video borescope. The control portion of the articulating guide tube may further include control means for controlling the articulating section and the video borescope therein.

As another aspect of the invention, a method for cooling a visual inspection device for use within an operating temperature environment, of a component being monitored, comprises the steps of: providing an inspection system including a compressed air supply, a video borescope and a cooling apparatus for cooling the video borescope; inserting the video borescope into the cooling apparatus; supplying compressed air to the cooling apparatus, in order to cool the video borescope; introducing the cooled video borescope, into the operating temperature environment; and controlling the video borescope, in order to conduct a visual inspection.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENT

The invention will be described as applied to the inspection of internal combustion turbine components, although it will become apparent that it could also be applied to inspect other types of power industry equipment, and to other applications (e.g., without limitation, automotive; aviation; surveillance; bomb squad).

As applied herein, "full-way" articulation refers to a video borescope inspection system that allows 360° viewing of, for example, combustion turbine components that exist in areas that require traveling around, through, or near other components.

As applied herein, "vortex cooler" refers to a vortex generating tube variously known as the "Ranque vortex tube," the "Hilsch tube," the "Ranque-Hilsch tube" and "Maxwell's Demon." A vortex cooler has no moving parts. Compressed air is supplied to an internal counter bore through tangential inlet nozzles. The nozzles turn the compressed air into a vortex or spinning airstream that passes down the tube in the form of a spinning shell, similar to a tornado. A second, cooler, inner airstream flows through the center of this outer spinning shell and transfers heat to the outer, spinning airstream in the form of kinetic energy. An exhaust valve at one end of the tube allows some of this heat to escape. What does not escape heads back down the tube as cold air. A detailed explanation of vortex coolers can be found in the publication "A Phenomenon of Physics: How the Vortex Tube Works," as published by EXAIR ® Corporation of 1250 Century Circle North, Cincinnati, Ohio 45246, which is explicitly incorporated herein by reference.

As employed herein "operating temperature environment" refers to the approximate operating temperature of the interior of, for example, the equipment component being inspected or monitored. For example, the operating temperature of a combustion turbine is approximately 800° F. (427° C.).

Figure 1:
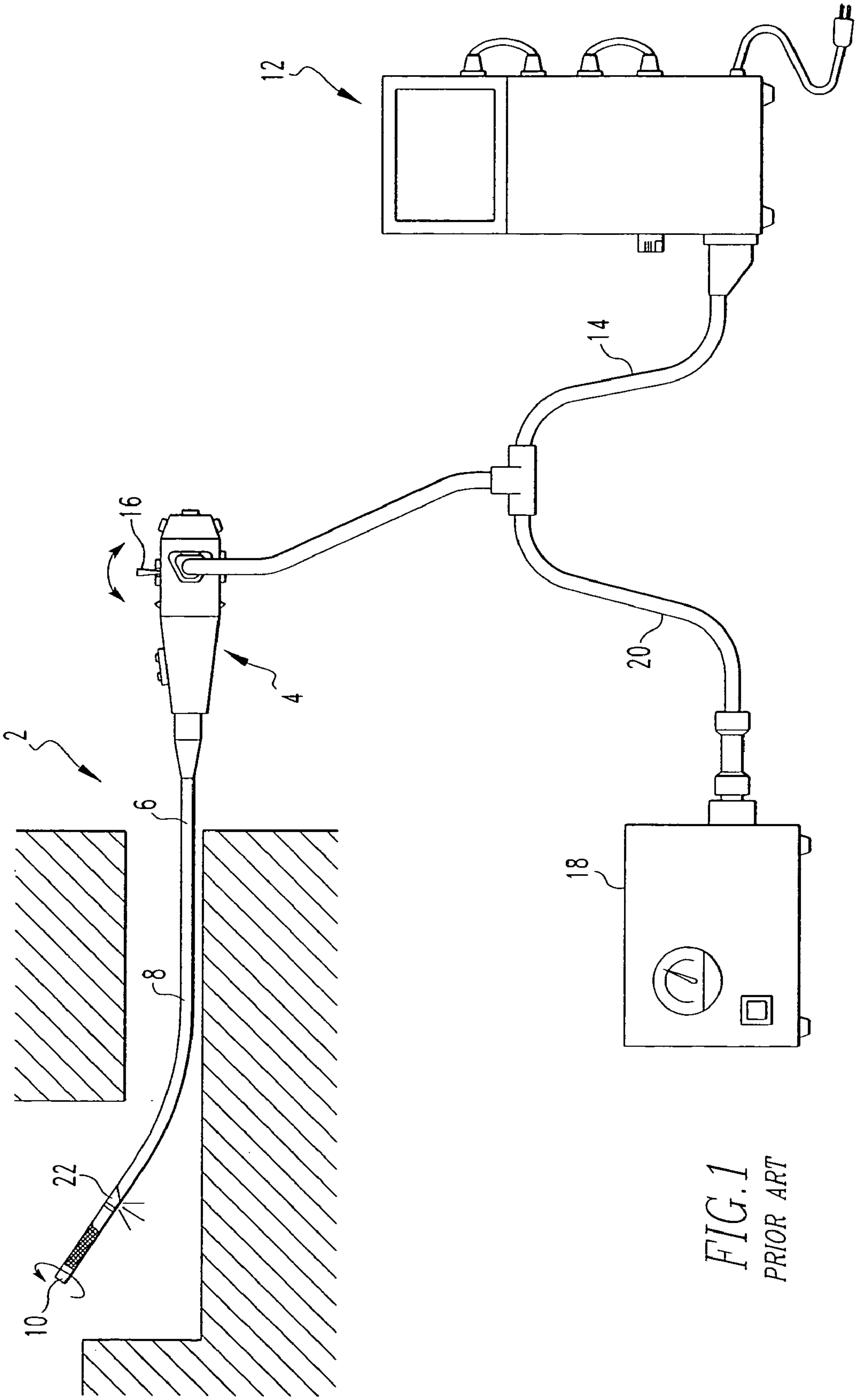
FIG. 1 PRIOR ART
FIG. 1 is a vertical elevational view of a visual inspection system employing an electronic borescope.
Figure 2:
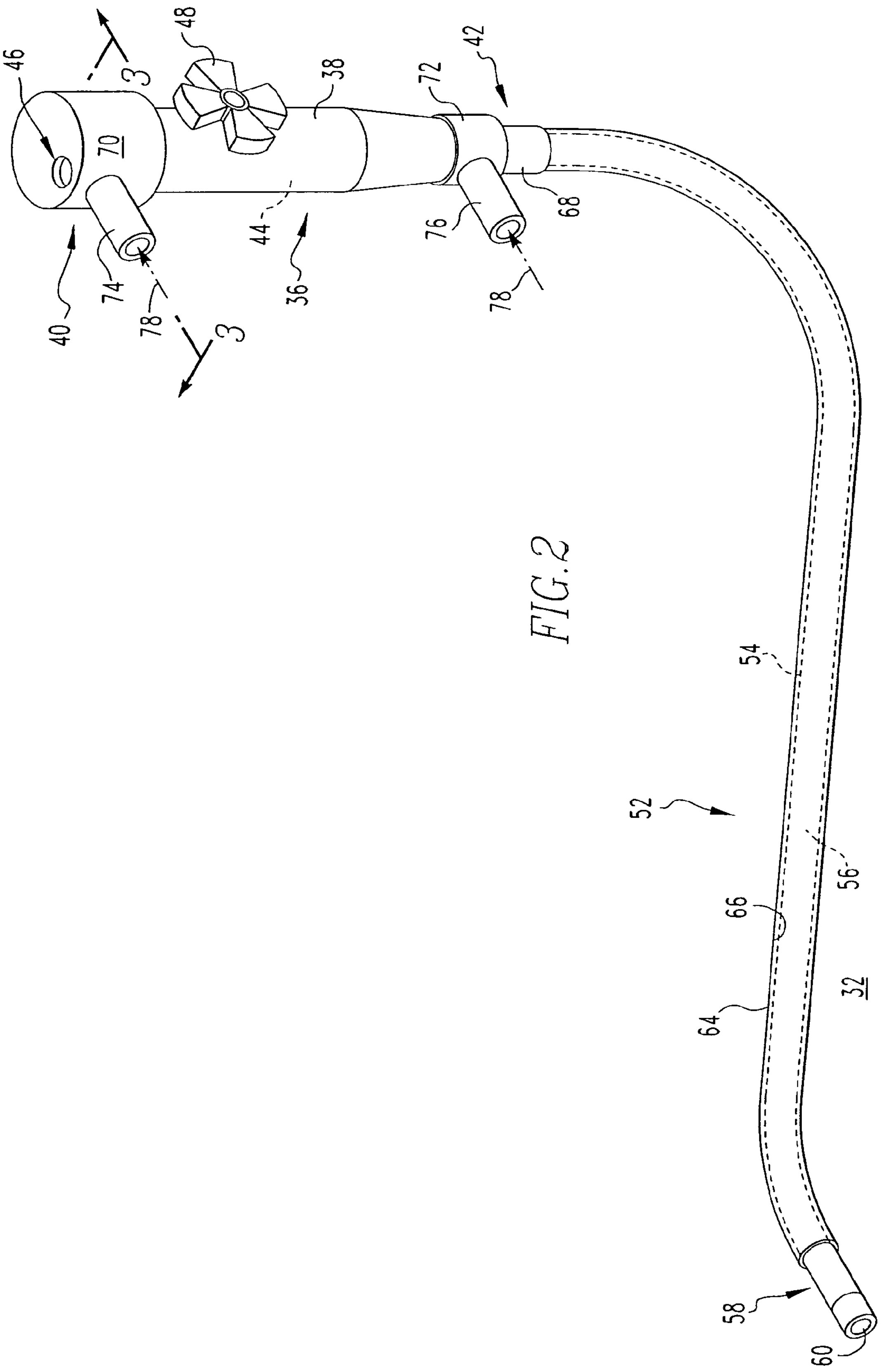
FIG. 2 is an isometric view of an inspection probe cooling apparatus, in accordance with the present invention.
Figure 3:
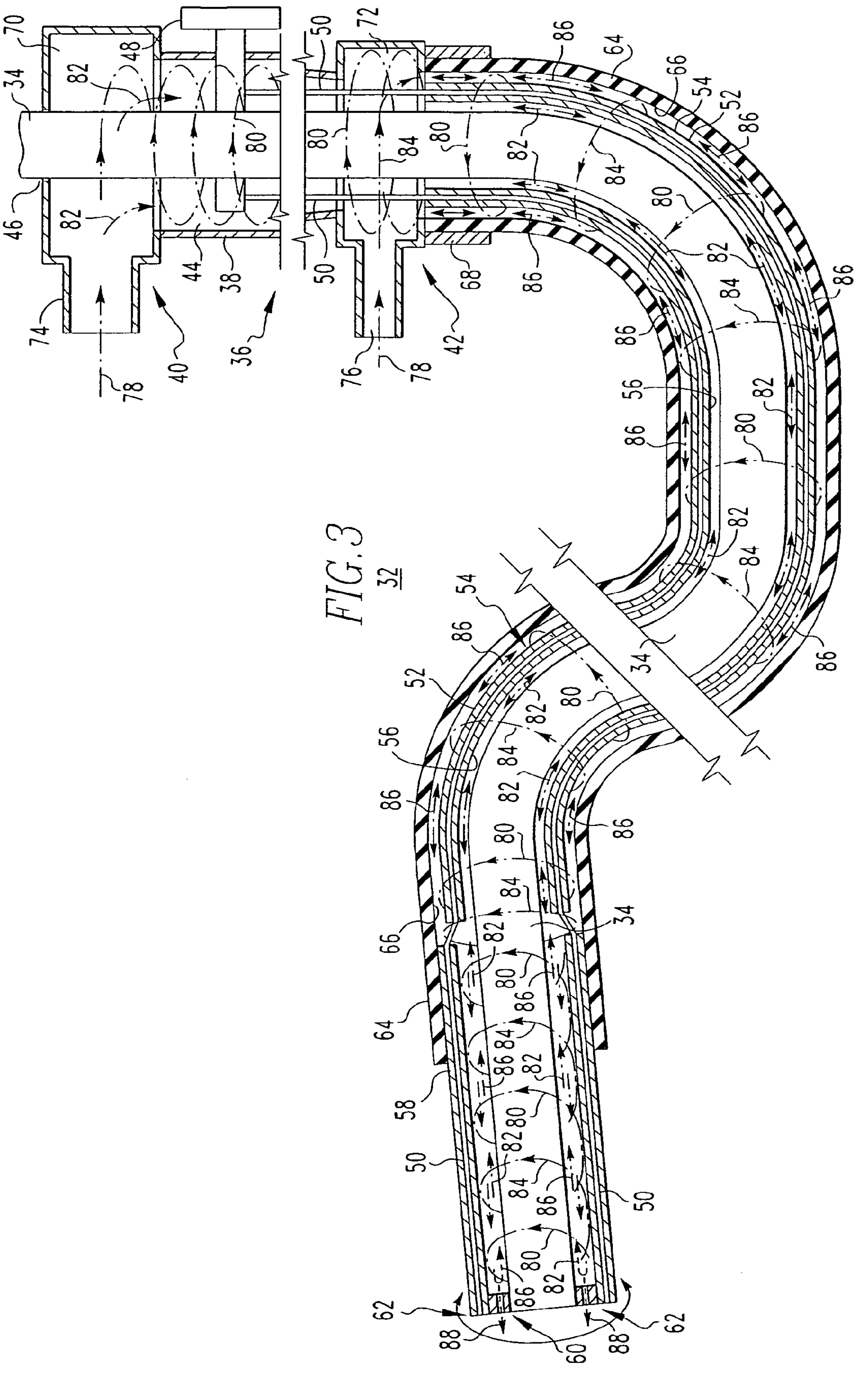
FIG. 3 is a cross-sectional view taken along line 3—3 of FIG. 2, and enlarged to show internal structures.
Figure 6:
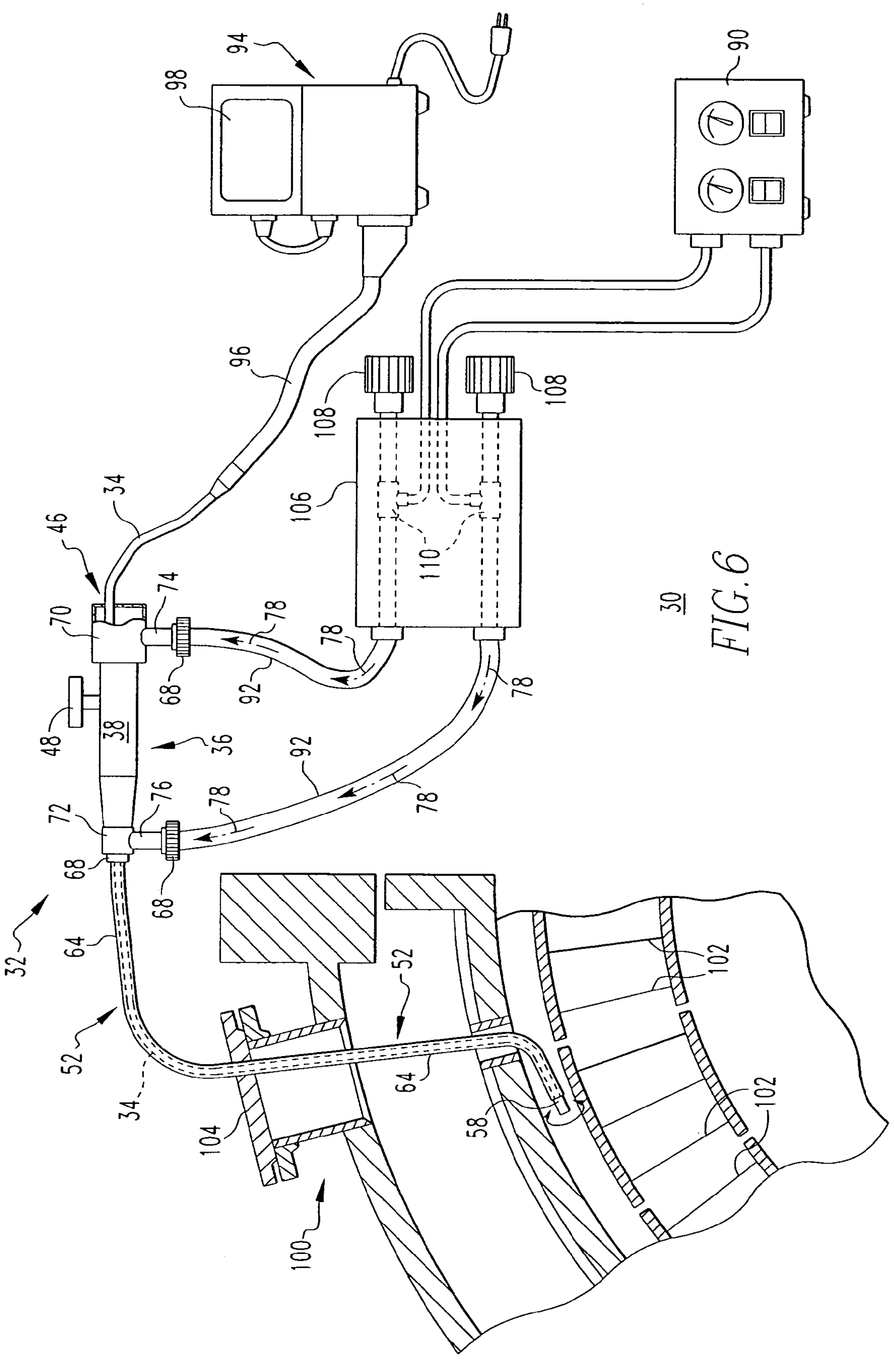
FIG. 6 is a vertical elevational view of a high-temperature inspection system as employed to inspect internal components of a combustion turbine in accordance with the present invention, and a cross-sectional schematic of the combustion turbine to show internal structures.

FIG. 2 illustrates a cooling apparatus 32 for an inspection probe, such as the video borescope 34 shown in FIGS. 3 and 6. As shown, the cooling apparatus 32 includes an articulating guide tube 36 having a control portion 38, an elongated flexible portion 52 and an articulating section 58. The control portion 38 includes a first end 40, a second end 42 and a first interior portion 44. The elongated flexible portion 52 includes an exterior 54 and a second interior portion 56. A thermal protective sleeve 64 surrounds the elongated flexible portion 52 of the articulating guide tube 36 and includes a third interior portion 66. An inlet 46 is formed within the first end 40 of the control portion 38 and is structured to receive the exemplary video borescope 34 (FIGS. 3 and 6), in order that the video borescope 34 may be guided down the first interior portion 44, through the second interior portion 56 and into the articulating section 58 of the articulating guide tube 36. At least one vortex cooler 70 (two are shown in FIG. 2), which is adapted to cool and circulate a compressed fluid, such as, for example, compressed air 78, as shown, cools both the articulating guide tube 36 and the video borescope 34 therein.

As shown, the exemplary cooling apparatus 32 includes first and second vortex coolers 70,72 proximate the first and second ends 40,42, respectively, of the control portion 38 of the articulating guide tube 36. The first and second vortex coolers 70,72 each include an inlet nozzle 74,76 for receiving the exemplary compressed air 78. The exemplary articulating section 58 of the articulating guide tube 36 forms an opening 60 through which the video borescope 34 can view (best shown in FIGS. 3, 4 and 5). The control portion 38 includes a control mechanism such as, for example, the exemplary control handle 48, in order to control the articulating section 58 and the video borescope 34 therein. A collar 68 attaches the exemplary thermal protective sleeve 64 to the second end 42 of the articulating guide tube 36.

As shown in FIG. 3, the exemplary video borescope 34 is inserted through inlet 46, guided down through the first interior portion 44 within control portion 38, down through the second interior portion 56 within the elongated flexible portion 52, and into the articulating section 58 of the articulating guide tube 36. The elongated flexible portion 52 of articulating guide tube 36 is surrounded by thermal protective sleeve 64 which attaches to both the second end 42 of the control portion 38 of articulating guide tube 36, and, the articulating section 58 of the articulating guide tube 36. A collar 68 connects the exemplary thermal protective sleeve 64 to the second end 42. However, it will be appreciated that any suitable fastening mechanism (e.g., without limitation, pipe clamps; press-fit relationship) (not shown), could alternatively be used to fasten the thermal protective sleeve 64 at these locations.

The exemplary articulating section 58 permits full-way articulation thereby providing 360° viewing or image capturing through the video borescope 34. The exemplary control handle 48 manipulates cables 50 (best shown in FIGS. 4 and 5) which are connected to the articulating portion 58. However, it will be appreciated that any suitable control mechanism (not shown) could be employed to control the articulating section 58 of the articulating guide tube 36. For example, an electronic or remote control mechanism (not shown) could be employed rather than the exemplary control handle 48.

Continuing to refer to FIG. 3, in operation, compressed air 78 is supplied to the first and second vortex coolers 70,72 through the first and second inlet nozzles 74,76, respectively. The first vortex cooler 70 forms a first outer rotating airstream 80 and a first cooler, inner airstream 82. The first cooler, inner airstream 82 is blown over the video borescope 34 and through the first and second interior portions 44, 56, respectively, of the articulating guide tube 36. The second vortex cooler 72 forms a second outer rotating airstream 84 and a second cooler, inner airstream 86. The second cooler, inner airstream 86 blows through the third interior portion 66 of the thermal protective sleeve 64 and over the exterior 54 of the elongated flexible portion 52 of the articulating guide tube 36.

All four airstreams 80,82,84,86 travel within the articulating guide tube 36 of the cooling apparatus 32 towards the articulating section 58. The first and second cooler, inner airstreams 82,86 transfer heat 88 to the first and second outer rotating airstreams 80,84, respectively. At least a portion of this heat 88 is exhausted through at least one exhaust vent 62 (best shown in FIG. 5, in which four exhaust vents 62 are shown). The exemplary exhaust vents 62 are disposed in the articulating section 58 of the articulating guide tube 36. However, it will be appreciated that any number of exhaust vents, located in any number of locations (not shown) and in any combination (not shown) along the articulating guide tube 36, could be employed to exhaust and regulate a portion of the compressed air, for example heat 88. After a portion of the warmer airstreams, for example outer rotating airstreams 80,84, is exhausted as heat 88, the first and second cooler, inner airstreams 82,86 having traveled down the cooling apparatus 32 towards the articulating section 58, are turned back as cold air and blown over the video borescope 34.

Figure 4:
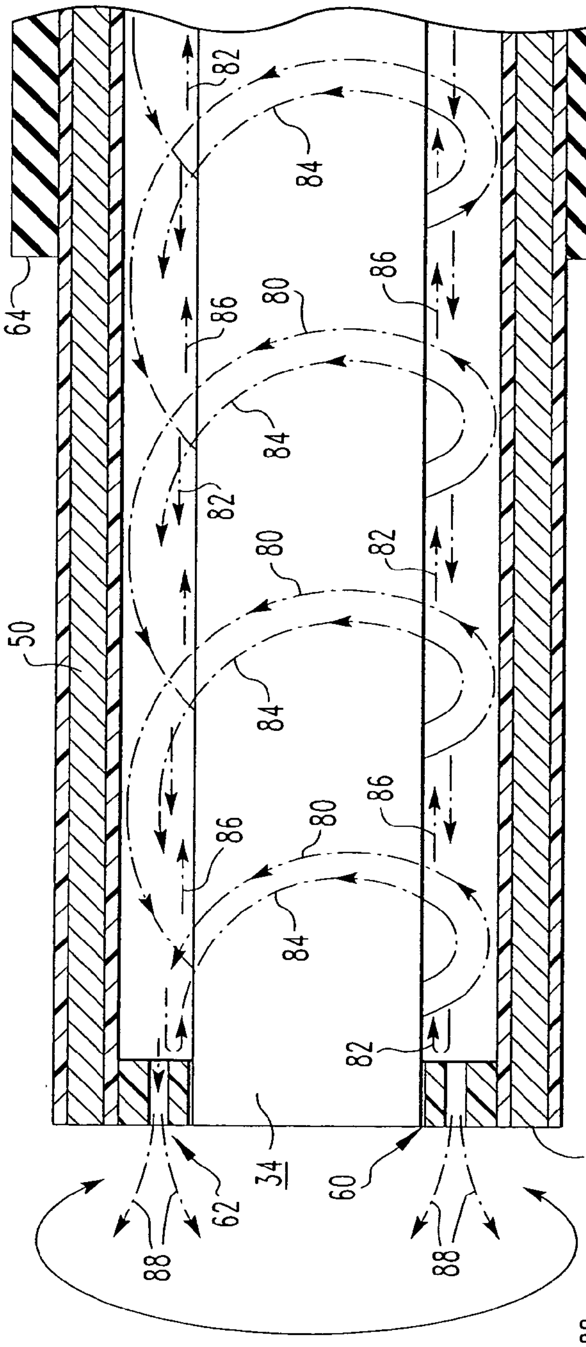
FIG. 4 is an enlarged cross-sectional view of the articulating section of the cooling apparatus of FIG. 2.

FIG. 4 illustrates the exemplary articulating section 58 of the cooling apparatus 32 (FIGS. 2 and 3). As shown, the exemplary video borescope 34 is housed within the articulating section 58 and views or captures images through an opening 60 therein. As discussed above, the first and second outer rotating airstreams 80,84 travel within the articulating section 58 towards the exhaust vents 62 (best shown in FIG. 5). The first and second cooler, inner airstreams 82,86 cool the video borescope 34 as they travel down the articulating section 58 and transfer heat 88 to the first and second outer rotating airstreams 80,84, which is then discharged or exhausted through the exhaust vents 62, as shown. The first and second cooler, inner airstreams 82,86 are turned back and continue circulating within the cooling apparatus 32 (FIG. 3) thereby continuously cooling the video borescope 34. The control cables 50 are connected to the exemplary control handle 48 (best shown in FIG. 3) and permit full-way articulation of the articulating section 58 and the video borescope 34 therein.

Figure 5:
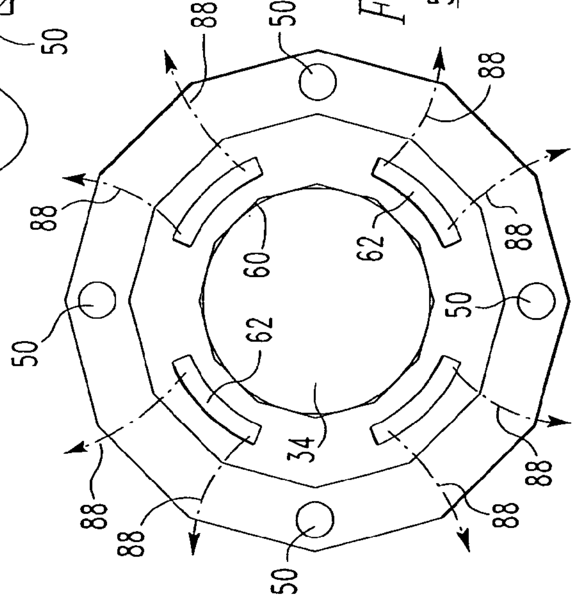
FIG. 5 is a plan view of the articulating section of FIG. 4.

FIG. 5 illustrates the end of the articulating section 58 of the articulating guide tube 36 (FIG. 3). As shown, the exemplary articulating section 58 includes four exhaust vents 62 through which heat 88 is exhausted as described above. Four cables 50 are employed to control articulation of the articulating section 58 and the video borescope 34 housed therein. However, it will be appreciated that any number or combination of exhaust vents 62 (not shown) and any number or combination of cables 50 or other suitable control mechanisms (not shown) could be alternatively employed.

FIG. 6 illustrates an inspection system 30 as employed to conduct a visual inspection of the internal components, for example, turbine blades 102 of a combustion turbine 100. As shown, the inspection system 30 includes a compressed fluid source, such as the air compressor 90 shown, which supplies a compressed fluid, such as, for example, compressed air 78. The inspection system 30 also includes a video borescope 34, an imaging processing system 94 for processing images viewed through the video borescope 34, and a cooling apparatus 32 for cooling the video borescope 34. For illustrative purposes, the exemplary high-temperature inspection system 30 and cooling apparatus 32 therefore will be described as used with the XL Pro VideoProbe ®, a video borescope 34 manufactured by Everst VIT, Incorporated of 199 U.S. Highway 206, Flanders, N.J. 07836. However, it will be appreciated that a wide array of visual inspecting probes and related equipment could alternatively be employed.

As shown, the exemplary video borescope 34 is connected to the image processing system 94 and monitor 98 by an electronic cable 96. It will be appreciated that images gathered by the video borescope 34 could alternatively be relayed or transmitted and viewed by remote, wireless signal (not shown) to any suitable alternative image processing system (not shown) such as, for example, a computer terminal (not shown) employing image processing software (not shown), as is well known in the art.

The inspection system 30 may optionally include a vortex container 106, as shown. The vortex container 106 provides additional and individual regulation of the compressed air 78 supplied to each of the cooling apparatus vortex coolers 70,72 by, for example, including at least one vortex cooler 110 (two are shown in FIG. 6) and at least one flow regulator 108 (two are shown in FIG. 6). The exemplary vortex container 106 includes two flow regulators 108, one for each compressed air supply hose 92. The flow regulators 108 may comprise, for example, a muffler (not shown), to bleed or exhaust a portion of the compressed air 78, and an adjustable handle mechanism, for adjusting or regulating this exhaust rate. However, it will be appreciated that any suitable flow regulating mechanism (not shown) could be employed as an alternative to the vortex container 106 and flow regulator 108 configuration illustrated in FIG. 6.

As employed, the video borescope 34 is inserted into the cooling apparatus 32 by way of the inlet 46. As described above, the video borescope 34 is then snaked or guided down through the control portion 38 of the articulating guide tube 36, through the elongated flexible portion 52 and into the articulating section 58 (best shown in FIG. 3). Compressed air 78 is then supplied to the cooling apparatus 32, in order to cool the video borescope 34 housed therein. The cooled video borescope 34, which is housed within the thermal protective sleeve 64, is then introduced into an environment having a temperature roughly equivalent to the operating temperature of the equipment or component being monitored, such as, for example, the inside of a combustion turbine 100 shortly after being shut down. The operating temperature of the interior of a combustion turbine 100, for example, shortly after shut down, can exceed about 800° F. (426° C.). However, it will be appreciated that the approximate operating temperature of 800° F. (426° C.) is meant to be illustrative only. The cooled video borescope 34 could be employed in a wide variety of environments (not shown) having a wide range of temperatures.

Continuing to refer to FIG. 6, the exemplary cooled video borescope 34 can be inserted through a combustion turbine inspection port 104 thereby eliminating the need to first disassemble the combustion turbine 100, in order to conduct the visual inspection. Once inserted within the turbine 100, the articulating section 58 and the video borescope 34 therein can then be controlled by, for example, the control handle 48, in order to conduct a visual inspection of internal components, such as, for example, turbine blades 102.

It will be appreciated that alternative compressed fluids (not shown) other than compressed air 78 could be employed and supplied by a compressed fluid source other than the exemplary air compressor 90. Moreover, while the exemplary air hoses 92 used to supply the compressed air 78 are attached to the first and second inlet nozzles 74,76 of the first and second vortex coolers 70,72, respectively, using collars 68, it will be appreciated that any alternative fastening mechanism (not shown) could be employed.

The exemplary thermal protective sleeve 64 is made from silicone rubber and has an interior lining of fiber glass (not shown). However, it will be appreciated that any suitable thermally insulating material (not shown) could alternatively be employed to thermally protect the video borescope, for example 34.

This novel inspection system 30 permits the immediate inspection within high-temperature environments, such as, for example, the interior of a combustion turbine 100 at approximately the operating temperature thereof. Such environments can reach temperatures in excess of 800° F. (427° C.). The exemplary cooling apparatus 32 is capable of maintaining a constant video borescope 34 operating temperature of approximately 150° F. (66° C.) for extended periods of time, within such environments. This new capability avoids undesirable lengthy and costly down times of power industry components when it is necessary to conduct visual inspections thereof. Additionally, as discussed above, it will be appreciated that the present invention may also provide improved inspection capabilities in a wide array of other applications both within and outside of the power industry field.

While specific embodiments of the invention have been described in detail, it will be appreciated by those skilled in the art that various modifications and alternatives to those details could be developed in light of the overall teachings of the disclosure. For example, it will be appreciated that any number of vortex coolers, for example 70,72 may be employed in any combination (not shown) to provide cooling for the visual inspection device, for example video borescope 34. Accordingly, the particular arrangements disclosed are meant to be illustrative only and not limiting as to the scope of the invention which is to be given the full breadth of the claims appended and any and all equivalents thereof.

What is claimed is:

1. A cooling apparatus for an inspection probe, said cooling apparatus comprising:

- an articulating guide tube having a control portion, an elongated flexible portion and an articulating section, said control portion including a first end, a second end and a first interior portion, said elongated flexible portion including an exterior and a second interior portion;
- a thermal protective sleeve surrounding said elongated flexible portion of said articulating guide tube and including a third interior portion;
- an inlet formed within the first end of said control portion and structured to receive said inspection probe, in order that said inspection probe may be guided down the first interior portion, through the second interior portion and into said articulating section of said articulating guide tube; and
- at least one vortex cooler adapted to cool and circulate a compressed fluid thereby cooling both said articulating guide tube and said inspection probe therein.

2. The cooling apparatus of claim 1 wherein said at least one vortex cooler includes a first vortex cooler, proximate the first end of said control portion of said articulating guide tube, and a second vortex cooler proximate the second end of said control portion of said articulating guide tube; wherein said first vortex cooler cools the first and second interior portions of said articulating guide tube and the inspection probe therein; and wherein said second vortex cooler cools the third interior portion of said thermal protective sleeve and the exterior of said elongated flexible portion of said articulating guide tube.

3. The cooling apparatus of claim 1 wherein each of said at least one vortex cooler further includes at least one inlet nozzle for receiving said compressed fluid; and wherein said articulating guide tube further includes at least one exhaust vent for regulating said compressed fluid.

4. The cooling apparatus of claim 3 wherein said compressed fluid includes compressed air supplied to each of said at least one vortex cooler through said at least one inlet nozzle.

5. The cooling apparatus of claim 4 wherein said at least one vortex cooler includes first and second vortex coolers proximate said first and second ends, respectively, of said control portion of said articulating guide tube; wherein said first vortex cooler forms a first outer, rotating airstream and a first cooler, inner airstream, said first cooler, inner airstream blowing over said inspection probe and through said first and second interior portions, respectively, of said articulating guide tube; wherein said second vortex cooler forms a second outer, rotating airstream and a second cooler, inner airstream, said second cooler, inner airstream blowing through said third interior portion of said thermal protective sleeve and over the exterior of said elongated flexible portion of said articulating guide tube; wherein said first and second cooler, inner airstreams transfer heat to said first and second outer rotating airstreams, respectively, and wherein at least a portion of said heat transferred to said first and second outer rotating airstreams is exhausted through said at least one exhaust vent in said articulating guide tube.

6. The cooling apparatus of claim 1 wherein said articulating section of said articulating guide tube forms an opening through which said inspection probe can view; and wherein said control portion of said articulating guide tube further includes control means for controlling said articulating section and said inspection probe therein.

7. The cooling apparatus of claim 6 wherein said articulating section and said opening therein provide full-way articulation to permit 360° viewing through said inspection probe.

8. The cooling apparatus of claim 1 wherein said inspection probe is a video borescope; and wherein said at least one vortex cooler and said thermal protective sleeve provide sufficient cooling for said video borescope, in order to permit continuous inspection operations within an operating temperature environment, of a component being monitored, for an extended period of time.

9. An inspection system comprising:

a compressed fluid source supplying a compressed fluid;

a video borescope;

an image processing system for processing images viewed through said video borescope; and a cooling apparatus for cooling said video borescope, said cooling apparatus comprising:

an articulating guide tube having a control portion, an elongated flexible portion and an articulating section, said control portion including a first end, a second end and a first interior portion, said elongated flexible portion including an exterior and a second interior portion;

a thermal protective sleeve surrounding said elongated flexible portion of said articulating guide tube and including a third interior portion;

an inlet formed within the first end of said control portion, said inlet receiving said video borescope, which passes down through the first interior portion, through the second interior portion and into said articulating section of said articulating guide tube; and at least one vortex cooler cooling and circulating said compressed fluid thereby cooling both said articulating guide tube and said video borescope therein.

10. The inspection system of claim 9 wherein each of said at least one vortex cooler further includes at least one inlet nozzle receiving said compressed fluid; and wherein said articulating guide tube further includes at least one exhaust vent regulating said compressed fluid.

11. The inspection system of claim 10 wherein said compressed fluid source includes at least one air compressor; wherein said compressed fluid is compressed air; and wherein each of said at least one air compressor includes at least one air hose feeding said compressed air through each of said at least one inlet nozzle and into said at least one vortex cooler.

12. The inspection system of claim 11 wherein said at least one vortex cooler includes first and second vortex coolers proximate said first and second ends, respectively, of said control portion of said articulating guide tube; wherein said first vortex cooler forms a first outer, rotating airstream and a first cooler, inner airstream, said first cooler, inner airstream blowing over said video borescope and through said first and second interior portions, respectively, of said articulating guide tube; wherein said second vortex cooler forms a second outer, rotating airstream and a second cooler, inner airstream, said second cooler, inner airstream blowing through said third interior portion of said thermal protective sleeve and over the exterior of said elongated flexible portion of said articulating guide tube; wherein said first and second cooler, inner airstreams transfer heat to said first and second outer rotating airstreams, respectively; and wherein at least a portion of said heat transferred to said first and second outer rotating airstreams is exhausted through said at least one exhaust vent in said articulating guide tube.

13. The inspection system of claim 9 wherein said articulating section of said articulating guide tube forms an opening for video borescope viewing therethrough; wherein said articulating section and said opening therein provide full-way articulation to permit 360° viewing through said video borescope; and wherein said control portion of said articulating guide tube further includes control means for controlling said articulating section and said video borescope therein.

14. The inspection system of claim 13 wherein said control means includes a control handle and at least one control cable connected to said articulating section of said articulating guide tube, in order to control said articulating section and said video borescope therein.

15. The inspection system of claim 9 further including a collar securing said thermal protective sleeve to the second end of said control portion of said articulating guide tube.

16. The inspection system of claim 9 wherein said at least one vortex cooler and said thermal protective sleeve provide sufficient cooling for said video borescope, in order to permit continuous inspection operations within an operating temperature environment, of a component being monitored, for an extended period of time.

17. The inspection system of claim 9 further including a vortex container connected between said compressed fluid source and said cooling apparatus, said vortex container including regulating means for further regulating said compressed fluid supplied to said cooling apparatus.

18. The inspection system of claim 17 wherein said regulating means includes at least one flow regulator for regulating said compressed fluid supplied to each of said at least one vortex cooler of said cooling apparatus.

* * * * *